US012691271B2

(12) United States Patent
Song et al.

(10) Patent No.: US 12,691,271 B2
(45) Date of Patent: Jul. 28, 2026

(54) MICRONEEDLE COMPRISING MICROFIBER NETWORK STRUCTURE

(71) Applicant: LG HOUSEHOLD & HEALTH CARE LTD., Seoul (KR)

(72) Inventors: Ji-Eun Song, Seoul (KR); Seung-Hyun Jun, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 744 days.

(21) Appl. No.: 18/013,828

(22) PCT Filed: Jun. 18, 2021

(86) PCT No.: PCT/KR2021/007700
§ 371 (c)(1),
(2) Date: Dec. 29, 2022

(87) PCT Pub. No.: WO2022/005071
PCT Pub. Date: Jan. 6, 2022

(65) Prior Publication Data
US 2023/0302266 A1    Sep. 28, 2023

(30) Foreign Application Priority Data

Jun. 30, 2020    (KR) ........................ 10-2020-0080091
Apr. 29, 2021    (KR) ........................ 10-2021-0055845

(51) Int. Cl.
*A61M 37/00*    (2006.01)
(52) U.S. Cl.
CPC . *A61M 37/0015* (2013.01); *A61M 2037/0023* (2013.01); *A61M 2037/0053* (2013.01)

(58) Field of Classification Search
CPC ...... A61M 37/0015; A61M 2037/0023; A61M 2037/0053
USPC ........................................................ 604/22
See application file for complete search history.

(56) References Cited

U.S. PATENT DOCUMENTS

| | | | |
|---|---|---|---|
| 2011/0098651 A1* | 4/2011 | Falo, Jr. ................ | A61L 31/148 604/173 |
| 2016/0129184 A1 | 5/2016 | Lee et al. | |
| 2019/0060205 A1 | 2/2019 | Jun et al. | |

FOREIGN PATENT DOCUMENTS

| | | | | |
|---|---|---|---|---|
| JP | 2016-189845 A | 11/2016 | | |
| KR | 10-2013-0006259 A | 1/2013 | | |
| KR | 10-2015-0005138 A | 1/2015 | | |
| KR | 10-2017-0103698 A | 9/2017 | | |
| WO | WO-2019103404 A1 * | 5/2019 | ........... | A61K 9/0021 |

OTHER PUBLICATIONS

International Search Report (PCT/ISA/210) issued in PCT/KR2021/007700, dated Sep. 17, 2021.

* cited by examiner

*Primary Examiner* — Phillip A Gray
(74) *Attorney, Agent, or Firm* — Birch, Stewart, Kolasch & Birch, LLP

(57)    ABSTRACT

The present disclosure relates to a microneedle comprising a microfiber network structure, and more specifically, relates to a microneedle which comprises an insoluble microfiber network structure comprised in a substrate portion of a dissolving microneedle, so that it can deliver a large amount of an aqueous solution of drugs to skin through a hole for drug injection on the back side of a patch without including drugs in the microneedle, also regardless of drug types.

8 Claims, 4 Drawing Sheets

[FIG. 1]
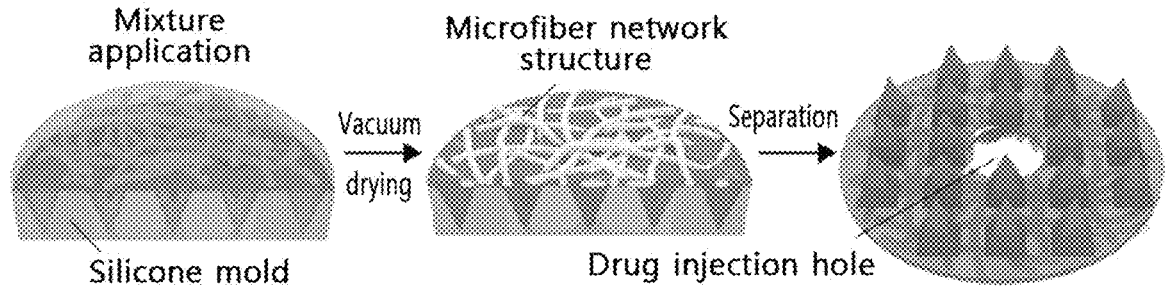
Mixture application — Silicone mold — Vacuum drying — Microfiber network structure — Separation — Drug injection hole
[FIG. 2]
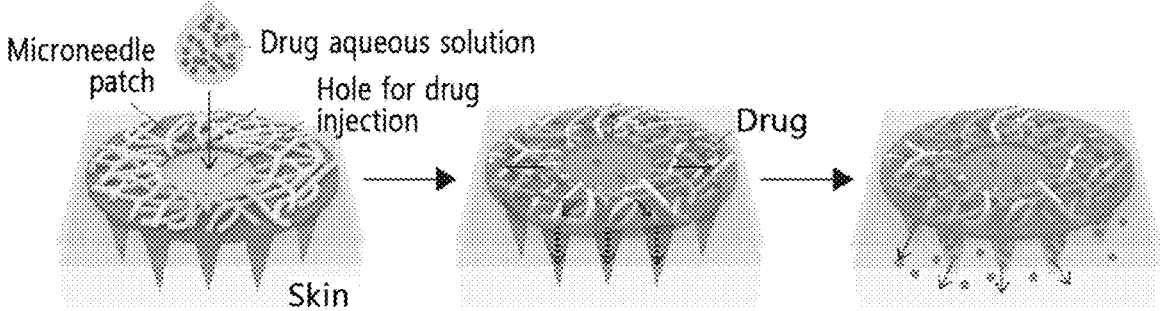
Microneedle patch — Drug aqueous solution — Hole for drug injection — Skin — Drug
[FIG. 3]
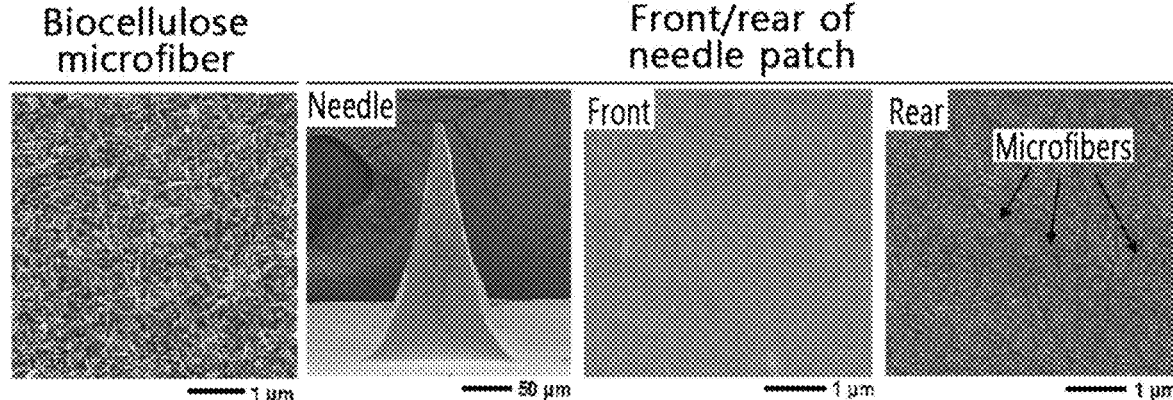
Biocellulose microfiber — Needle — Front/rear of needle patch — Front — Rear — Microfibers 【FIG. 4】
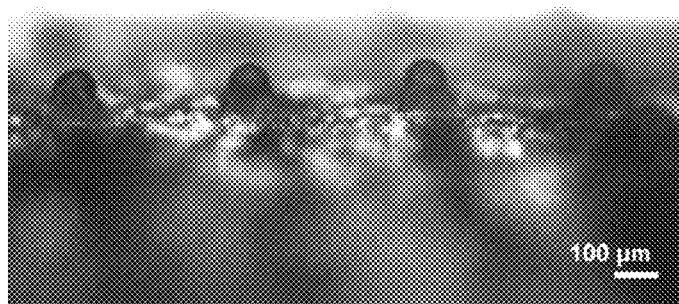
【FIG. 5】
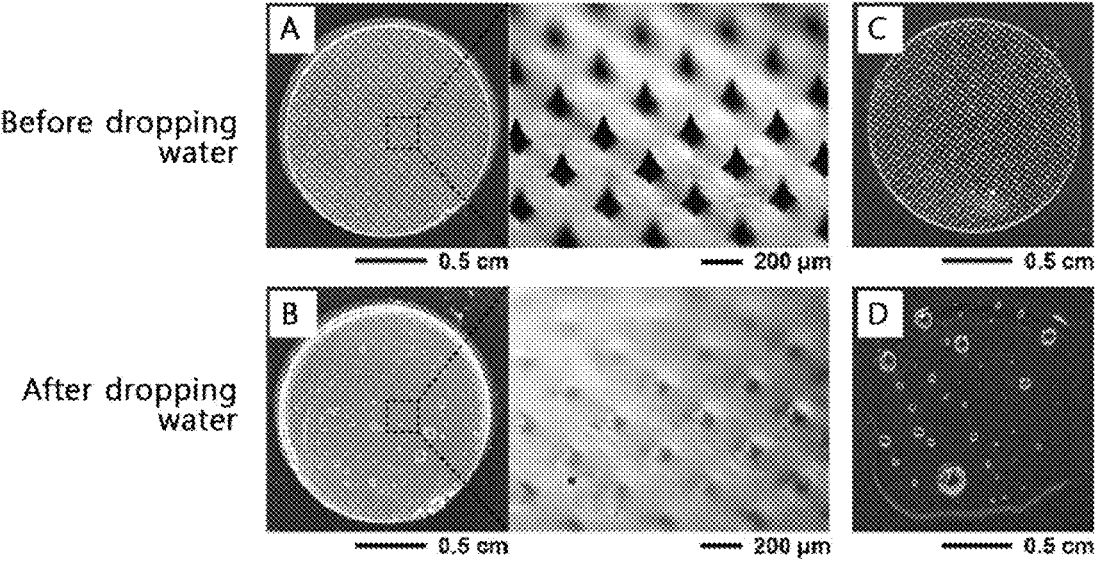

[FIG. 6]
Example 1                    Comparative example 2
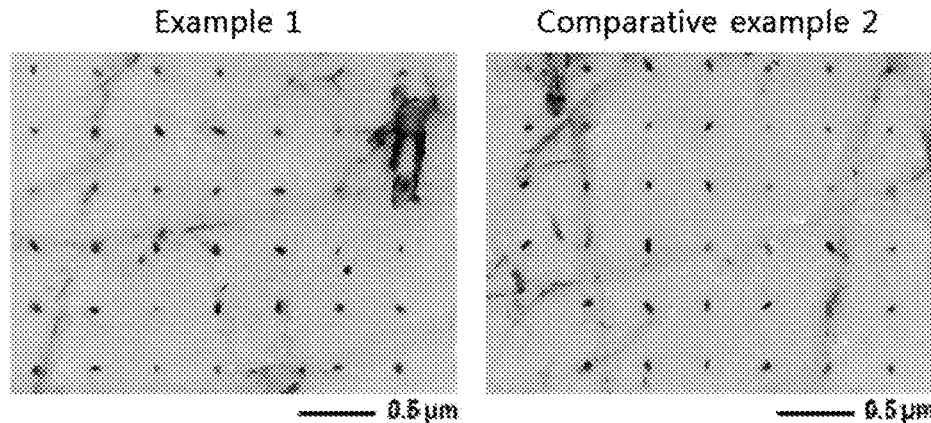
[FIG. 7]
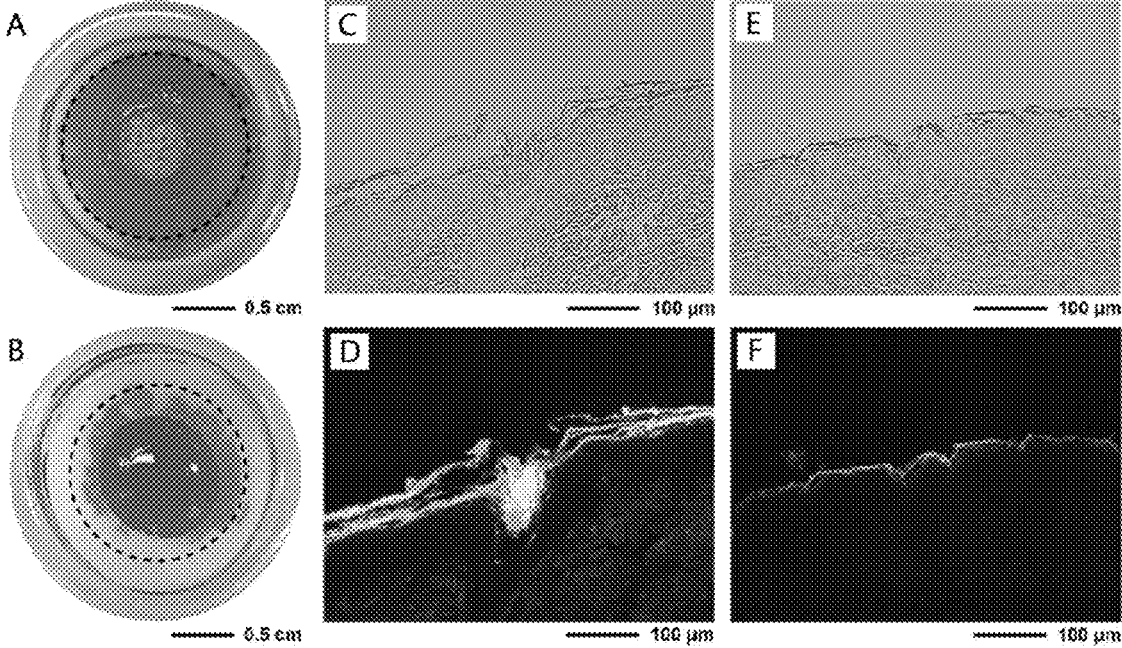

【FIG. 8】
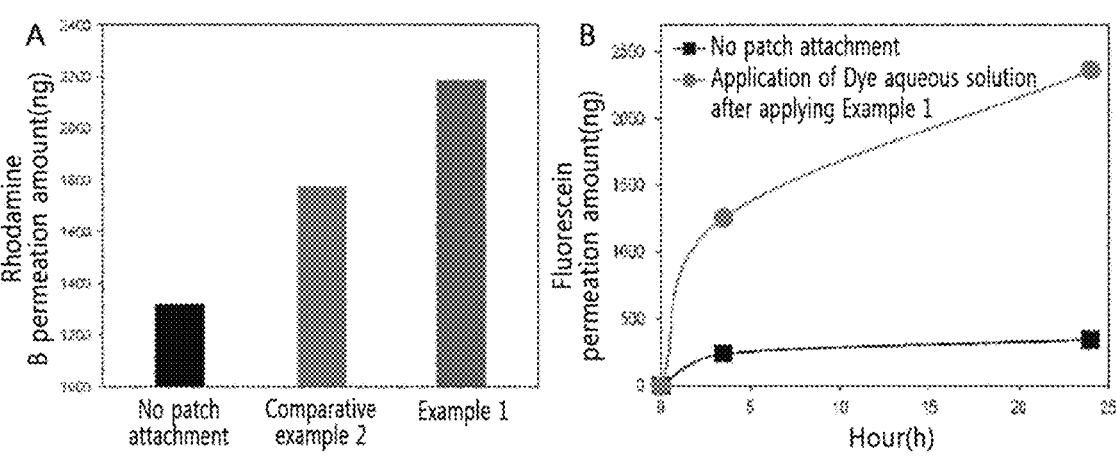

MICRONEEDLE COMPRISING MICROFIBER NETWORK STRUCTURE

TECHNICAL FIELD

The present application claims the priority based on Korean Patent Application No. 10-2020-0080091 filed on Jun. 30, 2020 and Korean Patent Application No. 10-2021-0055845 filed on Apr. 29, 2021, and the entire contents disclosed in the description and drawings of the corresponding applications are incorporated in the present application by reference.

The present disclosure relates to a microneedle patch containing a microfiber network structure.

BACKGROUND ART

In a transdermal drug delivery system, keratin, the outermost layer of skin with a thickness of 10 to 15 micrometers, acts as the most important barrier. A microneedle with a length of several hundred micrometers can physically penetrate the skin with minimal invasion, and can effectively deliver a drug to skin easily and painlessly, so it has been widely studied in various fields such as cosmetics and biomedicine. Starting with development of silicone microneedle prepared by semiconductor processing technology by U.S. Georgia Institute of Technology Prausnitz Group in 1998, various solid microneedles made of metal, ceramic or glass create temporary microchannels in skin to deliver a drug coated on a needle or a drug topically applied to skin. However, there is a problem that inflammation may cause a reaction, when the needle is broken in skin or things like small particles remain in the body. On the other hand, a dissolving microneedle made of a water-soluble polymer is prepared by containing a drug, and the drug is released as the needle is dissolved after it penetrates the skin. It has various advantages that it can be easily prepared compared to the solid microneedle and there is no problem of residue on skin, but the active compound which can be supported is limited to hydrophilic materials. In addition, since the microneedle has a size of several hundred micrometers and the amount of drug that can be supported therein is limited, only a small amount of drug can be delivered, so this may be insufficient to give efficacy. Furthermore, in the process of preparing a microneedle, there is a problem in that unstable active materials are denatured.

Therefore, several studies have been reported to improve a drug loading amount of the dissolving microneedle. A study was reported in which increases the drug delivery efficiency compared to single use of the needle, by loading the same drug to the dissolving microneedle and topical formulation, respectively, to apply the topical formulation, and then applying the needle (See Non-patent documents 1, 2). In addition, a system that simultaneously delivers two phases of drug and horse oil by applying horse oil to the edge of a dissolving microneedle patch containing a hydrophilic drug has been reported. However, the above methods also did not significantly improve the drug delivery amount, and there is a great inconvenience in use, such as having to apply a needle after a formulation applied to skin is properly dried, or having to apply an oil phase to a needle and then applying it to skin, and the like.

Numerous references are referenced throughout the present description and citations thereof are indicated. The disclosures of the cited documents are incorporated in the present description by reference in their entirety to more clearly describe the level of the art to which the present disclosure pertains and the content of the present disclosure.

PRIOR ART DOCUMENTS

Patent document 1: Korean Patent Publication No. 10-2017-0103698

Non-patent document 1: Molecular pharmaceutics 14 (2017) 2024-2031

Non-patent document 2: Journal of cosmetic dermatology 18 (2019) 1083-1091

Non-patent document 3: Journal of cosmetic dermatology 18 (2019) 936-943

DISCLOSURE

Technical Problem

Accordingly, in order to solve the problems, in the present disclosure, it has been confirmed that various kinds of drugs additionally supplied after skin perforation by the microneedle patch not only can be quickly spread according to the network structure formed by the microfiber structure, but also can be delivered into skin in a large amount deep in the skin in the entire area of the patch, when a microneedle patch is prepared by adding an insoluble microfiber network structure into a dissolving microneedle, thereby completing the present disclosure.

Thus, an object of the present disclosure relates to a microneedle containing a microfiber network structure, and more specifically, is to provide a microneedle which contains an insoluble microfiber network structure based on a dissolving microneedle, so that it can deliver a large amount of an aqueous solution to skin through a hole for drug injection on the back side of a patch without including a drug in the needle, also regardless of the drug type.

More specifically, an object of the present disclosure is to provide the following embodiments.

Embodiment 1

A microneedle comprising a microfiber network structure; and a microneedle forming material.

Embodiment 2

The microneedle according to Embodiment 1, wherein the microfiber forming the network structure is at least one selected from the group consisting of cellulose fiber, acrylic fiber, chitosan fiber, polyethylene fiber, polypropylene fiber, polyethylene terephthalate fiber, polyimide fiber and polyamide fiber.

Embodiment 3

The microneedle according to any one of the preceding embodiments, wherein the microneedle comprises a needle portion in which a plurality of needles are formed and a substrate portion to which the plurality of needles are attached, and the microfiber network structure is comprised in the substrate portion.

Embodiment 4

The microneedle according to any one of the preceding embodiments, wherein the microfiber network structure is not comprised in the needle portion.

Embodiment 5

The microneedle according to any one of the preceding embodiments, wherein the microneedle forming material is swollen or dissolved in skin.

Embodiment 6

The microneedle according to any one of the preceding embodiments, wherein the microneedle forming material comprises a water-soluble polymer.

Embodiment 7

The microneedle according to any one of the preceding embodiments, wherein the microneedle forming material comprises at least one selected from the group consisting of hyaluronic acid or salts thereof, carboxymethyl cellulose or salts thereof, vinyl pyrrolidone-vinyl acetate copolymers, poly vinyl alcohols, poly vinyl pyrrolidone and sugars.

Embodiment 8

The microneedle according to any one of the preceding embodiments, wherein the content of the microfiber network structure comprised in the microneedle is 0.01% by weight or more but less than 13.6% by weight based on the total weight of the microneedle.

Embodiment 9

The microneedle according to any one of the preceding embodiments, wherein a drug injection hole is formed in the substrate portion of the microneedle.

Embodiment 10

The microneedle according to any one of the preceding embodiments, wherein the drug is spread over the entire area of the microneedle patch by the microfiber network structure comprised in the substrate portion, when the drug is injected through the drug injection hole.

Embodiment 11

The microneedle according to any one of the preceding embodiments, wherein the microfiber network structure is an oxidized biocellulose microfiber network water dispersion.

Embodiment 12

The microneedle according to any one of the preceding embodiments, wherein in the oxidized biocellulose, 0.8 mmol/g cellulose or more of cellulose among all alcohol groups comprised in the biocellulose before oxidation is substituted with a carboxyl group.

Embodiment 13

A microneedle kit comprising the microneedle according to any one of the preceding embodiments and a separately equipped drug.

Embodiment 14

A method for efficiently injecting an active ingredient to skin for a cosmetic purpose, comprising preparing the microneedle according to any one of the preceding embodiments; and injecting an active ingredient through a drug injection hole formed in the substrate portion of the microneedle.

Other objects and advantages of the present disclosure will become more apparent from the following detailed description of the invention, claims and drawings.

Technical Solution

One aspect of the present disclosure is to provide a microneedle comprising a microfiber network structure; and a microneedle forming material.

As a means for solving the problem, a microneedle patch was prepared by a micromolding method which is a conventional preparation method of a dissolving microneedle, by mixing a dissolving microneedle forming material with a microfiber network structure which is insoluble in water.

Since the microfiber network structure has an intertwined network structure in the three dimension, so it cannot enter the mold cavity forming a needle portion and is evenly dispersed only in the back part of the substrate portion, and thus, a bilayer microneedle patch comprising (i) a needle portion in which a plurality of needles swollen or dissolved by moisture in skin and (ii) a substrate portion in which an insoluble microfiber network structure is impregnated in a microneedle forming material is prepared.

In other words, the needle portion consists only of water-soluble components, while the substrate portion is not dissolved in water due to the microfiber network structure and play a reservoir role capable of immediately absorbing a drug aqueous solution injected into a hole for solution injection on the back side of the substrate portion and continuously delivering it to the microneedle. In addition, it was confirmed that the needle portion of the substrate bottom part was simultaneously dissolved in the fluid in skin and drug aqueous solution and formed a flow path, and a large amount of drug could penetrate into skin quickly along the flow path. Consequently, a system capable of delivering a large amount of drug, without any effort such as drug stability maintenance and pre-treatment processes (e.g.: drug surface modification and coating) for loading a drug into the microneedle.

Thus, the present disclosure provides a microneedle patch which is a microneedle comprising a needle portion in which a plurality of needles are formed and a substrate portion to which the plurality of needles are attached, and the microfiber network structure is comprised in the substrate portion, in which the microfiber network structure is comprised in the substrate portion and is not comprised in the needle portion.

In a preferable embodiment, in the substrate portion of the microneedle, a drug injection hole may be formed, and when a drug is injected through the drug injection hole, an effect of spreading the drug over the entire area of the microneedle patch can be obtained by the microfiber network structure comprised in the substrate portion.

In the microneedle patch of the present disclosure, one with the diameter of the microfiber forming the network structure of 1 nm to 100 nm or less, preferably, 20 nm to 80 nm, may be used. In addition, a polymer fiber, a carbon fiber, a conductive polymer fiber and the like which have an aspect ratio of 4 to 5000 are comprised, but not necessarily limited thereto.

Since the function to rapidly absorb a drug aqueous solution is reduced, when the content of the microfiber is less than 0.01 wt % of the dry weight of the microneedle patch, and preparation of a needle with a pointed tip is difficult, when 13.6% or more is added, the content of the microfiber network structure is preferably 0.01 wt % or more and less than 13.6 wt %.

The microfiber forming the network structure preferably means a fiber which is water-dispersible or is modified to be water-dispersible, and for example, at least one selected from the group consisting of cellulose fiber, acrylic fiber, chitosan fiber, polyethylene fiber, polypropylene fiber, polyethylene terephthalate fiber, polyimide fiber and polyamide fiber may be used, but not necessarily limited thereto.

Preferably, the microfiber network structure may be an oxidized biocellulose microfiber network water dispersion, which has high water absorption capacity and water retention capacity and is insoluble. The biocellulose is a cellulose microfiber synthesized from bacteria, and it has a thin fiber diameter and has excellent properties such as high physical strength, high crystallinity, and the like, compared to plant-derived cellulose, but it mainly has a gel or sheet-like shape, so it is difficult to apply to cosmetic formulations and the like. The present inventors have developed a biocellulose microfiber water dispersion capable of water dispersion by substituting an alcohol group of biocellulose in Patent document 1 with a carboxyl group.

Therefore, if biocellulose is used as the microfiber forming the microfiber network structure, oxidized biocellulose where some or all of alcohol groups are substituted with carboxyl groups should be used, and preferably at least 0.8 mmol of alcohol groups per gram of cellulose may be substituted with carboxyl groups among the total alcohol groups comprised in the biocellulose.

When non-oxidized general biocellulose is used, aggregates are formed in a water-soluble material (microneedle forming material) due to strong hydrogen bonds between fibers and a network structure cannot be formed. In other words, when non-oxidized general biocellulose is used, a network structure cannot be formed, and thus, it is impossible to form a needle, or a problem in that it enters the needle portion and leaves a residue on skin.

In the microneedle of the present disclosure, the microneedle forming material may be swollen or dissolved in skin, and for example, it may comprise water-soluble polymers such as hyaluronic acid or salts thereof, carboxymethyl cellulose or salts thereof, vinyl pyrrolidone-vinyl acetate copolymers, poly vinyl alcohols and poly vinyl pyrrolidone and the like; sugars such as xylose, sucrose, maltose, lactose, trehalose and the like; or a mixture thereof, but not limited thereto.

More specifically, the microneedle forming material is a water-soluble material which can be swollen or dissolved in skin, and may comprise hyaluronic acid or salts thereof, carboxymethyl cellulose or salts thereof, vinyl pyrrolidone-vinyl acetate copolymers, polyvinyl alcohols, polyvinyl pyrrolidone, sugars or a mixture thereof In addition, the microneedle forming material may additionally comprise a plasticizer, a surfactant, a preservative and the like, in consideration of the skin penetration strength of the microneedle, dissolution rate in skin, and the like.

As the plasticizer, for example, polyols such as ethylene glycol, propylene glycol, dipropylene glycol, butylene glycol, glycerin and the like may be used alone or in combination.

Furthermore, the microneedle comprising a microfiber network structure; and a microneedle forming material of the present disclosure may further comprise a drug inside. In other words, the present disclosure does not exclude the case of comprising a drug inside the dissolving microneedle as in before.

The structure and shape of the microneedle of the present disclosure is in a form in which the width of the base is narrowed from a wide place, when viewed from the base to the tip, and any shape such as a rectangular pyramid shape, a triangular pyramid shape, a stepped pyramid shape, a microblade shape, a bullet shape and the like is all possible, and the length preferably has a size within the range of 20 μm to 2 mm, but not limited thereto.

Another aspect of the present disclosure is to provide a microneedle kit comprising the microneedle and a separately equipped liquid drug.

Other aspect of the present disclosure is to provide a method for efficiently injecting a cosmetic drug into skin for cosmetic purposes, comprising: a step of manufacturing a microneedle comprising a substrate portion including a microfiber network structure and a microneedle forming material; a step of forming a drug injection hole in the substrate portion; and a step of injecting a cosmetic drug through the drug injection hole formed in a substrate portion of the microneedle.

The microneedle patch containing a microfiber network structure provided in the present disclosure plays a reservoir role which allows the microfiber to immediately absorb an injected drug solution and continuously deliver it to the microneedle, when a drug (preferably, drug aqueous solution) is injected through a drug injection hole on the back side of the patch, and thus, it can deliver a large amount of drug to skin through a microchannel formed by the microneedle dissolved by the body fluid and drug solution. In addition, since the drug is not supported in the needle, the drug is not denatured or there is no limitation in the supported amount in the preparation process of the needle, so it can be usefully applied to cosmetic or pharmaceutical industries.

All components described in the present disclosure, preferably, do not exceed the maximum use value stipulated in relative laws and regulations (for example, regulations on cosmetic safety standards, and the like (Korea), cosmetic safety technical standards (China)) and the like of Korea, China, U.S., Europe, Japan and the like. In other words, preferably, the microneedle of the present disclosure, and a drug to be used according to the present disclosure, and the microneedle kit comprising the drug comprises the components according to the present disclosure within the content limit allowed by relative laws and regulations of various countries.

Advantageous Effects

When a microneedle is prepared by adding a microfiber network structure to a water-dissolving microneedle forming material, the microfiber structure cannot enter into the mold cavity forming the needle and is evenly distributed only in the back part of the substrate portion, since it has a network structure that is intertwined with each other in the three dimension, and therefore, a microneedle patch having a dual structure of a water-soluble needle portion and an insoluble substrate portion can be provided even by one casting using a molding technique, which is a conventional preparation method of a microneedle.

On the other hand, when a drug injection hole is formed on the back side of the substrate portion of the microneedle of the present disclosure and a drug is injected through this, the microfiber plays a reservoir role of quickly absorbing the drug and continuously delivering it into the microneedle portion, and thus, a large amount of drug can be delivered into skin through a microchannel formed from the microneedle swollen or dissolved by moisture in the skin.

In addition, when a drug injection hole is formed on the back side of the substrate portion and the drug is injected through this, it is not necessarily required to include the drug in the needle, and therefore, there is an effect of solving the problem that the drug is denatured during the preparation process of the microneedle, or the drug loading amount is limited due to the size of the microneedle.

BRIEF DESCRIPTION OF THE DRAWINGS

FIG. 1 is a schematic diagram showing the preparation process of the microneedle patch containing a microfiber network structure.

FIG. 2 is a schematic diagram showing the drug delivery principle of the microneedle patch containing a microfiber network structure.

FIG. 3 is photographs showing the microstructure of the microfiber network structure according to one embodiment of the present disclosure and the microneedle patch prepared by Example 1.

FIG. 4 is a shape of the microneedle patch prepared by Comparative example 1.

FIG. 5 is photographs showing the difference in dissolution in water and structural properties of Example 1 and Comparative example 2.

FIG. 6 is the result of confirming the skin perforation rate of the microneedle by applying Example 1 and Comparative example 2 into pig skin.

FIG. 7 is the result of confirming the horizontal/vertical delivery of the drug, when Example 1 and Comparative example 2 are attached to pig skin and a model drug aqueous solution is applied.

FIG. 8 is the result of analyzing the skin permeation amount of the drug, when Example 1 and Comparative example 2 are attached to pig skin and a model drug aqueous solution is applied.

MODE FOR INVENTION

Hereinafter, the present disclosure will be described in more detail by examples. These examples are intended to illustrate the present disclosure more specifically only, and it will be obvious to those skilled in the art to which the present disclosure pertains that the scope of the present disclosure is not limited by these examples.

EXAMPLE

Experimental Example 1. Preparation of Microneedle Patch Containing Microfiber Water Dispersion Network The composition of the mixture for synthesizing a microneedle patch was a water-insoluble substance (Aqua Cellulose Solution™, provided by The Garden of Natural Solution), a water-soluble substance (hyaluronic acid), carboxymethyl cellulose, trehalose, glycerin, and distilled water (see Table 1). The Aqua Cellulose Solution™ contains 1.5% of an aqueous dispersion of biocellulose microfibers, 95.5% of distilled water, and 3% of hexanediol, in which the alcohol groups of biocellulose are substituted with carboxyl groups so that it can be dispersed in water. This mixture was applied to a silicone mold, and vacuum was held for 30 minutes, and then it was dried at 50 degrees for 3 hours. The dried patch was separated from the mold and a hole for drug injection with a diameter of 6 mm was drilled in the center of the patch (See FIG. 1).

TABLE 1

| Materials | Example 1 | Comparative example 1 | Comparative example 2 |
|---|---|---|---|
| Hyaluronic acid | 2.2 | 2.2 | 2.2 |
| Carboxylmethyl cellulose | 1.8 | 1.2 | 2.55 |
| Trehalose | 3.0 | 3.0 | 3.0 |
| Glycerin | 2.3 | 2.3 | 2.3 |
| Aqua Cellulose Solution ™ | 50.0 | 91.4 | 0 |
| Distilled water | up to 100 | up to 100 | up to 100 |
| Preparation or not | ○ | X | ○ |
| Weight of microfiber in final patch (%) | 7.5 | 13.6 | 0 |

In Table 1 above, Example 1 is the microneedle patch containing a microfiber water dispersion network (7.5% based on dry weight).

Comparative example 1 is the microneedle patch containing a microfiber water dispersion network (13.6% based on dry weight).

Comparative example 2 is the dissolving microneedle patch not containing a microfiber water dispersion network.

The scanning electron microscope photographs of the microneedle patch prepared in Example 1, including scanning electron microscope photographs showing the structure of the biocellulose microfibers used in Example 1 and Comparative example 1, were shown in FIG. 3. As confirmed in FIG. 3, it could be confirmed that when measuring the microstructure of the microneedle patch prepared in Example 1, the microfiber was hardly observed on the surface of the needle and the front of the patch, but the microfiber had an evenly distributed dual structure in the entire area on the rear of the patch (See FIG. 3).

In addition, it was confirmed that the weight of the biocellulose microfiber capable of preparing a microneedle patch (capable of forming a microneedle tip well) should be less than 13.6%, and when it is added more than that, the sharp tip of the needle was not formed and therefore it could not be used (See Comparative example 1 of Table 1 and FIG. 4).

Experimental Example 2. Confirmation of Structural Properties of Microneedle Patch Containing Microfiber In order to compare the structure and dissolution properties of the microneedle patch containing the microfiber prepared in Experimental example 1 (Example 1) and the microneedle patch not comprising microfiber (Comparative example 2), a change in the shape was observed by dropping a small amount of water (0.1 mL) to each patch before drilling a hole for drug injection. As a result, it was confirmed that in case of Comparative example 2, the entire patch comprising the needle was dissolved in water and the shape disappeared (See C and D of FIG. 5), whereas in Example 1, only the needle part was dissolved and the shape of the patch substrate portion was maintained (See A and B of FIG. 5).

Experimental Example 3. Comparison of Skin Perforation Rate of Microneedle Patches Containing and not Containing Microfiber The microneedle patch containing the microfiber prepared in Experimental example 1 (Example 1) and the microneedle patch not comprising a microfiber (Comparative example 2) were attached to pig skin, respectively, and after applying a force of 20 N for 10 seconds, the patch was removed and the microchannel produced on the skin was stained with a trypan blue aqueous solution to compare the skin perforation rate. As a result, the skin perforation rate was shown as 90% or more regardless of whether the microfiber was comprised or more (See FIG. 6).

Experimental Example 4. Visualization of Drug Delivery Ability of Microneedle Patch Containing Microfiber The microneedle patch containing the microfiber prepared in Experimental example 1 and the microneedle patch not comprising a microfiber (Comparative example 2) were attached to pig skin, respectively, and a model drug, rhodamine B aqueous solution (300 µg/mL, 100 µL) was injected into the hole structure of the patch to compare the horizontal distribution of the drug aqueous solution. It could be confirmed that rhodamine B was distributed only in a part of the microneedle patch in Comparative example 2 (See FIG. 7 B), whereas rhodamine B was evenly distributed over the entire patch area in Example 1 (See FIG. 7A). In addition, after applying fluorescein aqueous solution (50 µ/mL, 2 mL) to pig skin to which Example 1 was applied and pig skin to which nothing was attached, respectively, the patch and residual solution were removed and the skin was sectioned to determine the vertical distribution of the drug. When a drug was applied without the microneedle patch, weak fluorescence of fluorescein was observed only on the pig skin surface (See E and F of FIG. 7), whereas in case of Example 1, strong fluorescence was observed deep in the skin (See C and D of FIG. 7). As a result, it was confirmed that the microneedle patch containing a microfiber could deliver a drug deep into the skin in the entire patch area.

Experimental Example 5. Evaluation of Skin Permeation Amount of Drug Utilizing Microneedle Patch Containing Microfiber Example 1 and Comparative example 2 prepared in Experimental example 1 above were attached to pig skin and a receptor was equipped on a Franz cell filled with phosphate-buffered saline (pH 7.4, Gibco). Rhodamine B aqueous solution (300 µg/mL, 100 µL), a model drug was injected into the hole structure of each patch, and the drug was permeated at 37 degrees and 50% relative humidity for 17 hours, and then the patch and unabsorbed solution were removed and the drug permeation amount into the skin and receptor was analyzed (See FIG. 8). In addition, after applying fluorescein aqueous solution (50 µg/mL, 2 mL) to pig skin to which Example 1 was applied and pig skin to which nothing was attached, respectively, the drug permeation amount was analyzed through the same process as above (See B of FIG. 8). As a result, a much higher amount of drug was delivered into the skin without supporting the drug in the needle, compared to that applied only with the model drug aqueous solution without attaching the patch. In addition, it could be confirmed that more drugs could be delivered also compared to Comparative example 2.

The invention claimed is:

1. A method of manufacturing a microneedle comprising:
   i) first mixing a microneedle forming material with oxidized biocellulose microfibers;
   ii) applying the mixture from (i) to a mold to form the microneedle, wherein the mold comprises a mold cavity to form a needle portion; and
   iii) separating the microneedle formed in (ii) from the mold,
   wherein the microneedle comprises the needle portion in which a plurality of needles are formed and a substrate portion to which the plurality of needles are attached,
   wherein in i), the oxidized biocellulose microfibers are intertwined in three dimensions to form a microfiber network structure that cannot enter the mold cavity to form the needle portion,
   wherein the substrate portion comprises the microfiber network structure,
   wherein in ii), the microfiber network structure is comprised in the substrate portion and not comprised in the needle portion,
   wherein some or all of alcohol groups of the oxidized biocellulose are substituted with carboxyl groups, and
   wherein the method provides the microneedle in one casting step.

2. The method according to claim 1, wherein the microneedle forming material is swollen or dissolved in skin.

3. The method according to claim 1, wherein the microneedle forming material comprises a water-soluble polymer.

4. The method according to claim 1, wherein the microneedle forming material comprises one or more selected from the group consisting of hyaluronic acid or salts thereof, carboxymethyl cellulose or salts thereof, vinyl pyrrolidone-vinyl acetate copolymers, poly vinyl alcohols, poly vinyl pyrrolidone and sugars.

5. The method according to claim 1, wherein the content of the microfiber network structure comprised in the microneedle is 0.01% by weight or more, but less than 13.6% by weight based on the total weight of the microneedle.

6. The method according to claim 1, wherein a drug injection hole is formed in the substrate portion of the microneedle.

7. The method according to claim 6, wherein when a drug is injected through the drug injection hole, the injected drug is spread over the entire area of the microneedle patch by the microfiber network structure comprised in the substrate portion.

8. The method according to claim 1, wherein in the oxidized biocellulose, 0.8 mmol/g cellulose or more of cellulose among all alcohol groups comprised in the biocellulose before oxidation is substituted with a carboxyl group.

* * * * *